United States Patent
Guo et al.

(10) Patent No.: US 12,419,236 B2
(45) Date of Patent: Sep. 23, 2025

(54) METHODS AND COMPOSITIONS FOR IMPROVED PLANT REGENERATION FROM MICROSPORE-DERIVED EMBRYOS

(71) Applicant: Monsanto Technology LLC, St. Louis, MO (US)

(72) Inventors: Ying Guo, Ballwin, MO (US); Daniel Jefferson Karcher, St. Louis, MO (US); Huachun Wang Larue, Chesterfield, MO (US); Huai Wang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 18/523,087

(22) Filed: Nov. 29, 2023

(65) Prior Publication Data
US 2024/0188502 A1    Jun. 13, 2024

Related U.S. Application Data

(60) Provisional application No. 63/430,998, filed on Dec. 7, 2022.

(51) Int. Cl.
*A01H 4/00* (2006.01)
*A01G 2/00* (2018.01)
*A01G 24/22* (2018.01)

(52) U.S. Cl.
CPC .............. *A01H 4/005* (2013.01); *A01G 2/00* (2018.02); *A01G 24/22* (2018.02)

(58) Field of Classification Search
CPC .......... A01H 4/00; A01H 4/002; A01H 4/008; A01H 4/005
See application file for complete search history.

(56) References Cited

U.S. PATENT DOCUMENTS

| | | | |
|---|---|---|---|
| 5,322,789 A | 6/1994 | Genovesi et al. | |
| 5,445,961 A * | 8/1995 | Genovesi | C12N 5/04 800/276 |
| 5,538,880 A | 7/1996 | Lundquist et al. | |
| 5,550,318 A | 8/1996 | Adams et al. | |
| 5,589,617 A | 12/1996 | Nehra et al. | |
| 7,521,237 B2 | 4/2009 | Gupta et al. | |
| 2005/0003415 A1 * | 1/2005 | Gupta | C12Q 1/68 435/6 |
| 2016/0286749 A1 | 10/2016 | Garcia Rojas et al. | |
| 2021/0207153 A1 | 7/2021 | Charne et al. | |

FOREIGN PATENT DOCUMENTS

WO    2021/221743    11/2021

OTHER PUBLICATIONS

Yadollahi et al. "Effects of carbon source, polyethylene glycol and abscisic acid on secondary embryo induction and maturation in rapeseed (Brassica napus L.) microspore-derived embryos," Acta Physiol. Plant (2011) 33:1905-1912.*
Huang et al. "Plant Regeneration from Microspore-derived embryos of Brassica Napus: Effect of embryo age, culture temperature, osmotic pressure, abscisic acid," In Vitro Cell. Dev. Biol. 27P:28-31, Jan. 1991.*
Prabhudesai et al., "A continuous culture system of direct somatic embryogenesis in microspore-derived embryos of Brassica juncea," Plant Cell Reports (1993) 12:289-292.*
International Search Report and Written Opinion regarding International App. No. PCT/US23/81555, mailed Apr. 30, 2024.
Gupta, et al., "Agonist, antagonist and signaling modulators of ABA receptor for agronomic and post-harvest management." Plant Physiology and Biochemistry, vol. 148, pp. 10-25, (2020).
Nemoto, et al., "Identification of new abscisic acid receptor agonists using a wheat cell-free based drug screening system." Sci Rep 8, 4268, (2018).
Park, et al., "Abscisic Acid Inhibits PP2Cs via the PYR/PYL Family of ABA-binding START Proteins." Science 324, 1068-1071, (2009).
"Pyrabactin" ChEBI ID No. 73159. ChEBI. Last modified Apr. 12, 2013, Accessed on Mar. 26, 2024. Retrieved from <https://www.ebi.ac.uk/chebi/searchld.do;?chebild=CHEBI:73159>.
"Synthetic chemical offers solution for crops facing drought." Phys.org. Published on Apr. 30, 2009, Accessed on Mar. 26, 2024. Retrieved from <https://phys.org/news/2009-04-synthetic-chemical-solution-crops-drought.html#google_vignette>.
Rodriquez. Invitation to Pay Additional Fees regarding International App. No. PCT/US23/81555, mailed Feb. 29, 2024.
Invitation to Pay Additional Fees regarding International App. No. PCT/US2023/081555, mailed Feb. 29, 2024.

* cited by examiner

*Primary Examiner* — Susan McCormick Ewoldt
(74) *Attorney, Agent, or Firm* — Dentons US LLP; Chunping Li

(57) ABSTRACT

The present disclosure provides novel methods and compositions for the maturation and regeneration of plantlets from microspore-derived embryos. The compositions provided include a liquid maturation composition comprising a first plant hormone and about 430 mM to about 880 mM of a monosaccharide solute, a disaccharide solute, or a polysaccharide solute. The methods provided include the steps of contacting a microspore-derived embryo with a liquid maturation medium for a time period sufficient to produce a matured microspore-derived embryo, transferring the matured microspore-derived embryo to a substrate, and regenerating the plantlet from the matured microspore-derived embryo.

23 Claims, 10 Drawing Sheets

METHODS AND COMPOSITIONS FOR IMPROVED PLANT REGENERATION FROM MICROSPORE-DERIVED EMBRYOS

CROSS-REFERENCE TO RELATED APPLICATIONS

This application claims the priority of U.S. Provisional Appl. Ser. No. 63/430,998, filed Dec. 7, 2022, the entire disclosure of which is incorporated herein by reference.

FIELD OF THE INVENTION

The present invention relates to the field of plant breeding and agricultural biotechnology. More specifically, the invention provides novel methods and compositions for the regeneration of plantlets from microspore-derived embryos and doubled haploid production.

BACKGROUND OF THE INVENTION

Plant regeneration from microspore-derived embryos is important for microspore culture and doubled haploid (DH) production in many important crop plants, however, plant regeneration is often inefficient, highly variable, and genotype-dependent.

The use of doubled haploids in plant breeding programs allows new inbred populations to be created from desired parents in one to two generations. Haploids (1n) contain only one set of chromosomes following meiosis in male or female gametes. Doubled haploids (2n) carry two identical sets of chromosomes, which were derived from a haploid. Doubled haploids become diploid through chromosome doubling of the haploid chromosome by chemical or spontaneous means. In contrast, ordinary diploids (2n) obtain two chromosomes through fertilization between male and female gametes. DH technology makes it possible to obtain pure 2n homozygous plants in a single generation, whereas it generally requires 6 or more generations of self-crossing or backcrossing in typical breeding schemes to obtain pure 2n homozygous plants. DH technology is a critical tool used to reduce breeding cycle time, improve heritability, and accelerate genetic gain. In addition, DH technology is also a useful tool for the quick production of homozygous plants from gene stacking, genome editing, cytoplasm and nuclear genome exchange, and trait integration protocols.

Canola and winter oilseed rape DH production relies primarily on a microspore culture-based methods, which consist of many steps, including donor $F_1$ plant care, bud preparation, microspore isolation, microspore-derived embryogenesis, microspore-derived embryo germination, and plant regeneration. Microspores that are produced from $F_1$ plants have already gone through meiosis and genetic recombination, and therefore DHs derived from the microspores of $F_1$ plants are segregating for different traits and are thus ideal for breeding selection. Despite intensive research efforts to improve the processes for canola and winter oilseed rape DH production over the past few decades, successful microspore culture-based DH production remains highly genotype-dependent. Many canola and winter oilseed rape genotypes, especially those that are relevant to commercial breeding, are recalcitrant to microspore culture and DH production processes, rendering DH production outcomes highly variable and unpredictable.

SUMMARY OF THE INVENTION

In one aspect, the present disclosure provides a method of generating a plantlet, the method comprising: (a) contacting a microspore-derived embryo with a liquid maturation medium for a time period sufficient to produce a matured microspore-derived embryo, wherein the maturation medium comprises a first plant hormone and about 430 mM to about 880 mM of a monosaccharide solute, a disaccharide solute, or a polysaccharide solute; (b) transferring the matured microspore-derived embryo to a substrate; and (c) regenerating the plantlet from the matured microspore-derived embryo. In specific embodiments, the maturation medium comprises a concentration of said solute or any combination thereof of about 430 mM, about 460 mM, about 520 mM, about 575 mM, about 650 mM, about 700 mM, about 750 mM, about 780 mM, about 810 mM, about 840 mM, about 860 mM, about 430 mM, or may be defined as comprising any possible range of concentration derivable therefrom. In one embodiment, the time period of treatment sufficient to produce the matured micropore-derived embryo is about 14 days to about 20 days. In further embodiments, the time period is defined as about 14 days, about 15 days, about 16 days, about 17 days, about 18 days, about 19 days, or about 20 days. In another embodiment, such a method comprises first contacting the microspore-derived embryo with the maturation medium when the microspore-derived embryo is at a torpedo stage to a cotyledon stage of development. In yet another embodiment, the method comprises transferring the matured microspore-derived embryo to the substrate when the matured microspore-derived embryo is at a cotyledon stage of development. In still yet another embodiment, the substrate is selected from the group consisting of a solid substrate, a soil substrate, an agar substrate, and a soilless substrate. In one embodiment, the method comprises transferring the matured microspore-derived embryo directly to a soil substrate or a soilless substrate. In another embodiment, the total time between first contacting the micropore-derived embryo with the maturation medium and obtaining the plantlet is about 40 days to about 50 days. In specific embodiments, the total time between first contacting the micropore-derived embryo with the maturation medium and obtaining the plantlet is defined as being, or not more than, about 40 days, about 41 days, about 43 days, about 45 days, about 47 days, about 49 days, or about 50 days.

In one embodiment, the first plant hormone is an abscisic acid agonist. Non-limiting examples of an abscisic acid receptor agonist include abscisic acid, an abscisic acid analog, an abscisic acid derivative, pyrabactin, julolidine and fluorine containing ABA receptor activator 1, and julolidine and fluorine containing ABA receptor activator 2. The concentration of the first plant hormone, in another embodiment, is about 1.0 mg/L to about 20.0 mg/L. In yet another embodiment, the monosaccharide solute, the disaccharide solute, or the polysaccharide solute is selected from the group consisting of glucose, fructose, galactose, sucrose, lactose, and mannose.

In another embodiment, the method comprises contacting a plurality of microspore-derived embryos with the liquid maturation medium for a time period sufficient to produce a matured microspore-derived embryo, wherein the maturation medium comprises a first plant hormone and about 430 mM to about 880 mM of a monosaccharide solute, a disaccharide solute, or a polysaccharide solute; (b) transferring at least one matured microspore-derived embryo to a substrate; and (c) regenerating at least one plantlet from the matured microspore-derived embryo. The concentration of the plurality of microspore-derived embryos, in yet another embodiment, is about 3 to about 70 or about 10 to about 30 microspore-derived embryos per mL maturation medium.

In yet another embodiment, the method comprises culturing the microspore-derived embryo in an induction medium prior to contacting a microspore-derived embryo with a liquid maturation medium for a time period sufficient to produce a matured microspore-derived embryo. The method, in still yet another embodiment, comprises contacting the microspore-derived embryo with a supplemented maturation medium prior to transferring the matured microspore-derived embryo to the substrate, wherein the supplemented maturation medium comprises a second plant hormone. In one embodiment, the method comprises contacting the microspore-derived embryo with the supplemented maturation medium for about 1 hour to about 72 hours or about 12 hours to about 36 hours prior to transferring to the substrate. The second plant hormone, in another embodiment, is an auxin. Non-limiting examples of auxins include indole-3-butyric acid, 2,4-dichlorophenoxy-acetic acid (2,4-D), 4-amino-3,5,6-trichloro-picolinic acid (picloram), indole-3-acetic acid (IAA), naphthalene acetic acid (NAA), 4-chlorophenoxy acetic acid or p-chloro-phenoxy acetic acid (4-CPA or pCPA), 2,4,5-trichloro-phenoxy acetic acid (2,4,5-T), 2,3,5-triiodobenzoic acid (TIBA), phenylacetic acid (PAA), and 3,6-dichloro-2-methoxy-benzoic acid (dicamba). In yet another embodiment, the concentration of the second plant hormone is about 1.0 mg/L to about 20.0 mg/L.

The substrate, in still yet another embodiment, is an agar substrate and the agar substrate comprises a plant growth regulator and about 40 mM to about 75 mM of a monosaccharide solute, a disaccharide solute, or a polysaccharide solute. Non-limiting examples of such saccharide solutes include glucose, fructose, galactose, sucrose, lactose, and mannose. In one embodiment, the agar substrate further comprises about 1.0% to about 1.6% agar. The concentration of the plant growth regulator, in another embodiment, is about 0.25 mg/L to about 1.0 mg/L. In yet another embodiment, the plant growth regulator is a gibberellic acid. Non-limiting examples of a gibberellic acid include GA1, GA3, GA4, and GA7. In still yet another embodiment, the method further comprises transferring the plantlet from the agar substrate to a soil substrate or to a soilless substrate. In one embodiment, the microspore-derived embryo is derived from a species of the genus *Brassica* or of the genus *Capsicum*.

In another aspect, the present disclosure provides a liquid maturation composition comprising: (a) a first plant hormone; and (b) about 430 mM to about 880 mM of a monosaccharide solute, a disaccharide solute, or a polysaccharide solute. In one embodiment, the first plant hormone is an abscisic acid receptor agonist. In another embodiment, the abscisic acid receptor agonist is selected from the group consisting of abscisic acid, an abscisic acid analog, an abscisic acid derivative, pyrabactin, julolidine and fluorine containing ABA receptor activator 1, and julolidine and fluorine containing ABA receptor activator 2. The concentration of the first plant hormone, in yet another embodiment, is about 1.0 mg/L to about 20.0 mg/L. In still yet another embodiment, the first plant hormone is abscisic acid, and the concentration of the abscisic acid is about 1.0 mg/L to about 20.0 mg/L, about 1.0 mg/L to about 12.0 mg/L, about 1.0 mg/L to about 10.0 mg/L, about 4.0 mg/L to about 6.0 mg/L, or about 5.0 mg/L. In one embodiment, the monosaccharide solute, the disaccharide solute, or the polysaccharide solute is selected from the group consisting of glucose, fructose, galactose, sucrose, lactose, and mannose. In another embodiment, the disaccharide solute is sucrose, and the concentration of the sucrose is about 430 mM to about 730 mM, about 515 mM to about 660 mM, or about 585 mM. The composition further comprises, in yet another embodiment, a second plant hormone. In still yet another embodiment, the second plant hormone is an auxin. Non-limiting examples of an auxin include indole-3-butyric acid, 2,4-dichlorophenoxy-acetic acid (2,4-D), 4-amino-3,5,6-trichloro-picolinic acid (picloram), indole-3-acetic acid (IAA), naphthalene acetic acid (NAA), 4-chlorophenoxy acetic acid or p-chloro-phenoxy acetic acid (4-CPA or pCPA), 2,4,5-trichloro-phenoxy acetic acid (2,4,5-T), 2,3,5-triiodobenzoic acid (TIBA), phenylacetic acid (PAA), and 3,6-dichloro-2-methoxy-benzoic acid (dicamba). In one embodiment, the concentration of the second plant hormone is about 1.0 mg/L to about 20.0 mg/L. In another embodiment, the second plant hormone is indole-3-butyric acid, and the concentration of the indole-3-butyric acid is about 1.0 mg/L to about 20.0 mg/L, about 1.0 mg/L to about 12.0 mg/L, about 1.0 mg/L to about 10.0 mg/L, about 4.0 mg/L to about 6.0 mg/L, or about 5.0 mg/L.

BRIEF DESCRIPTION OF THE DRAWINGS

FIG. 1A shows photograph of a microspore culture plate having less than about 200 microspore-derived embryos. FIG. 1B shows a photograph taken with the dissecting scope of the same plate shown in FIG. 1A at the time of embryo dilution. FIG. 1C shows a photograph of micropore culture plate having about 800 microspore-derived embryos. FIG. 1D shows a photograph taken with the dissecting scope of the same plate shown in FIG. 1C at the time of embryo dilution. FIG. 1E shows a photograph of micropore culture plate having more than about 1000 microspore-derived embryos. FIG. 1F shows a photograph taken with the dissecting scope of the same plate shown in FIG. 1E at the time of embryo dilution.

FIG. 3A shows plantlets immediately following the transfer. FIG. 3B shows plantlets grown for one week after transfer to the soil mix.

FIG. 5A illustrates a typical side view of plantlets scored as a "0," "1," or "2" following culture in contact with a plant regeneration medium for about 4 weeks. FIG. 5B shows typical survival results for plantlets scored as a "0" following transfer to soil. FIG. 5C shows typical survival results for plantlets scored as a "1" following transfer to soil. FIG. 5D shows typical survival results for plantlets scored as a "2" following transfer to soil.

FIG. 8A shows plantlets regenerated using a culture-based method approximately 30 days after transfer (DAT). FIG. 8B shows plantlets regenerated using a culture-free method approximately 30 DAT.

DETAILED DESCRIPTION

Figure 1:
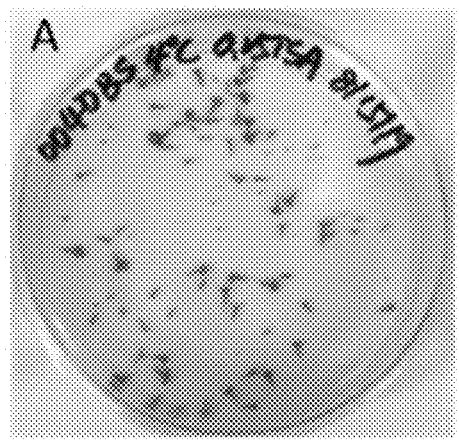
FIG. 1. Shows microspore-derived embryo plates following about 14 to about 20 days of microspore culture initiation.
Figure 1:
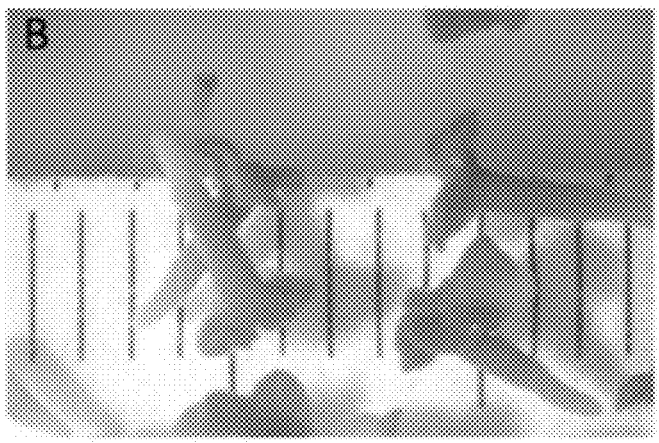
Figure 1:
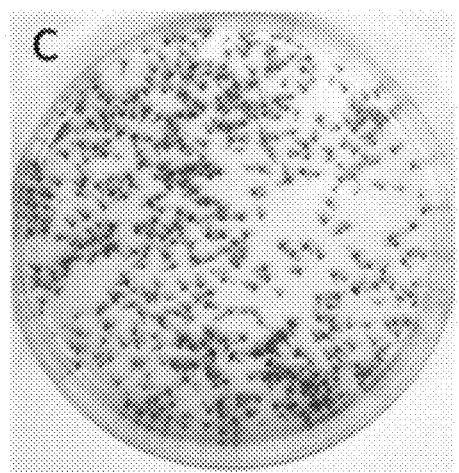
Figure 1:
Figure 1:
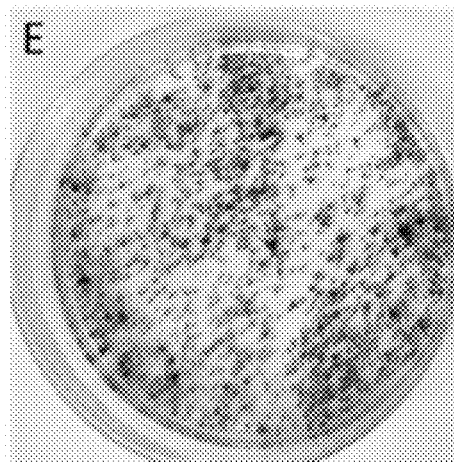
Figure 1:
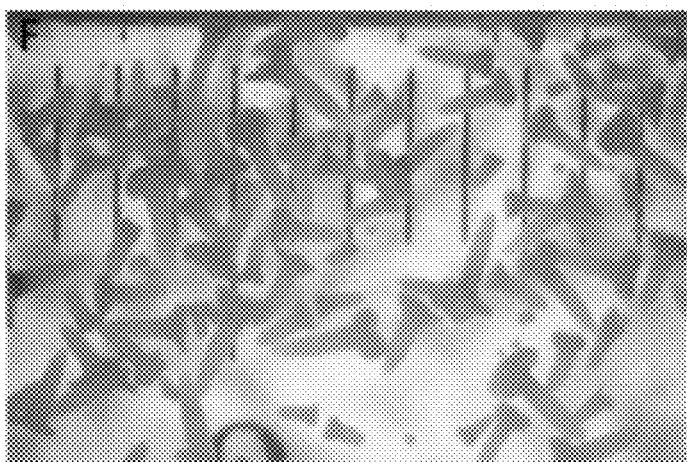

Doubled haploid (DH) plants are a valuable tool to plant breeders, particularly for generating inbred lines. A great deal of time is saved using DH processes, as homozygous lines are essentially produced in a single generation, negating the need for multigenerational conventional inbreeding, thus accelerating breeding genetic gain. In addition, DH plants are entirely homozygous, thus there is no allele masking effect between genotype and phenotype. Doubled haploids are very amenable to breeding selection and quantitative genetics studies. For breeders, DH populations have been particularly useful in QTL mapping, cytoplasmic conversions, and trait introgression.

Canola and winter oilseed rape DH production is a microspore culture-based process which consists of many steps and takes up to 9-12 months with current protocols. Although many improvements have been made over the last few decades, it is still a relatively inefficient and highly variable process with unpredictable production outcome. The present disclosure represents a significant advance by providing methods and compositions that dramatically improve DH production in canola and winter oilseed rape, leading to a dramatic increase in plant regeneration from microspore-derived embryos. Furthermore, the compositions and methods provided herein can be used for microspore culture-based DH production processes in other species propagated by microspore culture. Non-limiting examples of such include broccoli, pepper, cauliflower, wheat, rice, soybean, cotton, and corn.

The compositions and methods of the present disclosure provide a significant advancement over the art by and improve the plant regeneration rate dramatically from an average of about 23% (winter oilseed rape) or about 30% (canola) to about 87% across several genotypes in both canola and winter oilseed rape. Furthermore, the methods and compositions provided can be used to regenerate plants from $DH_0$ microspore-derived embryos without utilizing a tissue-culture step on solid media, thus shortening the cycle time to $DH_1$ seed set by up to 6 weeks. These compositions and methods can also be used to reduce the labor and resource input required to produce $DH_1$ seed set by 50% or more compared to traditional culture-based methods.

Embryogenesis and Doubled Haploids

Microspore-derived embryogenesis or initiation is a unique process in which haploid, immature pollen (microspores) are induced by one or more stress treatments to form embryos in culture. As used herein the term "micropore" refers to a collection of cells which are in the stages of stages of pollen development following the meiosis of pollen mother cells. The stages of pollen development are described and well known in the art (Fletcher et al., 1998; Kott et al., 1988). As used herein the term "microspore-derived embryo" refers to an embryo that was derived from microspore through tissue culture. As used herein the term "tissue culture" refers to composition comprising isolated cells of the same or of a different type or a collection of such cells organized into parts of a plant. Exemplary types of tissue cultures are protoplasts, calli, and plant cells that are intact in plants or parts of plants, such as embryos, pollen, flowers, leaves, roots, root tips, anthers, and the like. Means for preparing and maintaining plant tissue cultures are well known in the art (U.S. Pat. Nos. 5,538,880; 5,550,318, 5,445,961 and 5,322,789), the entire disclosure each of which is incorporated herein by reference.

Microspore culture is valuable process for DH production, and consists of two major processes: 1) embryogenesis/initiation; and 2) regeneration of plants from microspore-derived embryos. Improved methods for microspore embryogenesis/initiation are described in WO 2021/221743, which is specifically incorporated herein by reference in its entirety. Over the past several decades, there have been extensive efforts to improve plant regeneration from microspore-derived embryos, however, plant regeneration efficiency is still often low and highly genotype dependent. Those microspore-derived embryos which fail to germinate or regenerate into plantlets can be categorized as follows: 1) those that do not germinate due to low quality or lack of intact embryo structures; 2) those that exhibit heavy callusing following transfer onto solid plant regeneration media; and 3) those that experience arrested development following initial germination on plates.

Detailed methods for improved microspore embryogenesis/initiation are described for example in WO 2021/221743, the entire disclosure of which is specifically incorporated herein by reference. In summary, methods for microspore-derived embryogenesis initiation may include, in some embodiments, a step of pretreating a plant composition, for example, organs such as flower buds containing microspores, under conditions which divert the microspores from gametophytic development to that of embryogenic development. The pretreatment may include, in certain embodiments, incubation of the plant composition, preferably flower buds, at a cold temperature, which is a stress factor. Microspores may, in particular embodiments, then be isolated from the buds in an isolation medium capable of maintaining microspore viability and embryogenic potential. These isolated microspores, in some embodiments, may then be exposed to an embryoid/callus promoting medium (such as NLN medium) that includes about 0.01 mg/L to about 0.5 mg/L of 6-BAP and about 100 mg/L of cefotaxime sodium salt, as an antimicrobial agent (Nitsch and Nitsch, 1967; Lichter, 1982; Charne and Beversdorf, 1988). The source of nitrate in this medium is potassium nitrate while L-glutamine, L-serine, and glutathione serve as sources for amino acids.

Microspore-derived haploid embryos can be converted to doubled haploid embryos through the use of chromosome doubling agents or through spontaneous doubling. In one aspect, a method of chromosome doubling provided herein comprises the use of colchicine. Colchicine may be used at concentrations of about 25 mg/L to about 1600 mg/L, however preferably at a concentration of about 200 mg/L to about 1000 mg/L. When colchicine is used, microspores are treated preferably at a temperature of about 32° C. for a duration of about 24 hours to about 72 hours. Colchicine may be substituted with any other doubling agent known in the art. Non-limiting examples of which include amiprophos-methyl, oryzalin, pronamide, and trifluralin. As used herein, when referring to chromosome count, "doubling"

refers to increasing the chromosome number by a factor of two. For example, a haploid nuclear genome comprising 10 chromosomes is doubled to become a diploid nuclear genome comprising 20 chromosomes. As another example, a diploid nuclear genome comprising 20 chromosomes is doubled to become a tetraploid nuclear genome comprising 40 chromosomes. Chromosome doubling can be confirmed by flow cytometry or other molecular biology techniques known in the art.

Regeneration of Plantlets from Microspore-Derived Embryos

As described herein, there is a continuing need in the art for improved methods and compositions for the maturation and regeneration of microspore-derived embryos. The present disclosure provides such methods and compositions. In one aspect the present disclosure provides a method of generating a plantlet, the method comprising: (a) contacting a microspore-derived embryo with a liquid maturation medium for a time period sufficient to produce a matured microspore-derived embryo, wherein the maturation medium comprises a first plant hormone and about 430 mM to about 880 mM of a monosaccharide solute, a disaccharide solute, or a polysaccharide solute; (b) transferring the matured microspore-derived embryo to a substrate; and (c) regenerating the plantlet from the matured microspore-derived embryo. The stages of microspore-derived embryo development are well-known in the art and described at least in Seeds: The Ecology of Regeneration in Plant Communities (p. 1-17), Editors: R. S. Gallagher, January 2014. The stages of embryo development may include, for example, a globular stage, a torpedo stage, and a cotyledon stage. The globular stage of microspore-derived embryo development may further be described as an early globular stage, a mid-globular stage, or a late globular stage. Similarly, the torpedo stage and the cotyledon stage of microspore embryo development may be further defined as early, mid, or late. As used herein, the term "matured microspore-derived embryo" refers to a microspore-derived embryo that has a further development stage than the stage of the microspore-derived embryo at the time of initial contact with liquid maturation medium. In certain embodiments, the method comprises first contacting the microspore-derived embryo with the maturation medium when the microspore-derived embryo is at a torpedo stage of development. The method comprises, in particular embodiments, transferring the matured microspore-derived embryo to the substrate when the matured microspore-derived embryo is at a cotyledon stage of development. In some embodiments, the time period of treatment sufficient to produce the matured microspore-derived embryo is about 14 days to about 20 days, about 14 days to about 16 days, about 15 days to about 19 days, about 15 days to about 18 days, about 15 days to about 17 days, about 14 days, about 15 days, about 16 days, about 17 days, about 18 days, about 19 days, or about 20 days, including all ranges derivable therebetween. In certain embodiments, the total time between first contacting the micropore-derived embryo with the maturation medium and obtaining the plantlet is about 30 days to about 60 days or about 40 days to about 50 days, including all ranges derivable therebetween. In certain embodiments, after exposure to maturation medium matured embryos can be stored from about 0 days to about 8 weeks in the maturation media in cold storage before transferring to a substrate for plantlets regeneration.

As used herein, the term "substrate" refers to any material which may support the regeneration of an embryo into a plantlet. Non-limiting examples of such substrates include, a solid substrate, a soil substrate, an agar substrate, and a soilless substrate. A "soilless substrate" as used here refers to a soilless growth media used to properly anchor and support plant root growth and further development. Soilless substrates may be used, for example, in hydroponic growth conditions. As used herein the term "regeneration or regenerating" refers to the process of growth of growing a plant or plant part from one or more plant cells or tissues of an embryo. In some embodiments, the matured microspore-derived embryo is transferred directly to a soil substrate or a soilless substrate. For example, a matured micropore derived embryo which is "transferred directly" to a soil or soilless substrate would not be subjected to any in vitro culturing techniques prior to the transfer.

In certain embodiments, the maturation medium may comprise about 300 mM to about 1000 mM, about 350 mM to about 950 mM, about 400 mM to about 900 mM, about 430 mM to about 880 mM, about 440 mM to about 880 mM, about 430 mM to about 730 mM, or about 515 mM to about 660 mM, or about 585 mM of a monosaccharide solute, a disaccharide solute, or a polysaccharide solute, including all ranges derivable therebetween. Any monosaccharide solute, disaccharide solute, or polysaccharide solute may be used according to the methods and compositions provided by the present disclosure. Non-limiting examples of such solutes include glucose, fructose, galactose, sucrose, lactose, and mannose. The monosaccharide solute, disaccharide solute, or polysaccharide solute may serve as a nutrient to the microspore-derived embryo. Furthermore, the osmotic pressure that the maturation medium exerts onto the microspore-derived embryo due to the concentration of the solute in the liquid maturation medium may further support embryo survival and development.

In some aspects, the first plant hormone may be any plant hormone which induces or supports embryo maturation. In certain embodiments, the first plant hormone is an abscisic acid receptor agonist, non-limiting examples of which include abscisic acid, an abscisic acid analog, an abscisic acid derivative, pyrabactin, julolidine and fluorine containing ABA receptor activator 1, and julolidine and fluorine containing ABA receptor activator 2. The concentration of the first plant hormone, in particular embodiments, may be from about 1.0 mg/L to about 20.0 mg/L, about 1.0 mg/L to about 15.0 mg/L, about 1.0 mg/L to about 10.0 mg/L, about 2.0 mg/L to about 8.0 mg/L, about 4.0 mg/L to about 6.0 mg/L, about 1.0 mg/L, about 2.0 mg/L, about 3.0 mg/L, about 4.0 mg/L, about 5.0 mg/L, about 6.0 mg/L, about 7.0 mg/L about 8.0 mg/L, about 9.0 mg/L, about 10.0 mg/L, about 11.0 mg/L, about 12.0 mg/L, about 13.0 mg/L, about 14.0 mg/L, about 15.0 mg/L, about 16.0 mg/L, about 17.0 mg/L, about 18.0 mg/L, about 19.0 mg/L, or about 20.0 mg/L, including all ranges derivable therebetween.

In certain aspects, the methods provided by the present disclosure include contacting a plurality of microspore-derived embryos with the liquid maturation medium. As used herein the term "plurality" refers to more than one. The plurality of microspore-derived embryos may be, in some embodiments, present in the liquid maturation medium at a desired concentration. If, for example, the initial concentration of the microspore-derived embryos in the liquid maturation medium is higher than the desired concentration, then, in particular embodiments, the microspore-derived embryos may be diluted. The desired concentration of microspore-derived embryos in the liquid maturation medium may be, in some embodiments, about 3 to about 70, about 5 to about 65, about 5 to about 50, about 5 to about 45, about 5 to about 40, about 5 to about 50, about 5 to about 45, about 5 to about 40, about 5 to about 35, about 5 to about 30, about 5 to about 25, about 10 to about 30, or about 10 to about 25 microspore-derived embryos per mL maturation medium, including all ranges derivable therebetween.

In particular aspects, the methods provided by the present disclosure further include contacting the microspore-derived embryo with a supplemented maturation medium prior to transferring the matured microspore-derived embryo to the substrate, wherein the supplemented maturation medium comprises a second plant hormone. The second plant hormone may be any hormone which induces or supports tissue specification or organ initiation. In one embodiment, the second plant hormone is an auxin, non-limiting examples of which include indole-3-butyric acid, 2,4-dichlorophenoxy-acetic acid (2,4-D), 4-amino-3,5,6-trichloro-picolinic acid (picloram), indole-3-acetic acid (IAA), naphthalene acetic acid (NAA), 4-chlorophenoxy acetic acid or p-chloro-phenoxy acetic acid (4-CPA or pCPA), 2,4,5-trichloro-phenoxy acetic acid (2,4,5-T), 2,3,5-triiodobenzoic acid (TIBA), phenylacetic acid (PAA), and 3,6-dichloro-2-methoxy-benzoic acid (dicamba). The concentration of the second plant hormone, in particular embodiments, may be from about 1.0 mg/L to about 20.0 mg/L, about 1.0 mg/L to about 15.0 mg/L, about 1.0 mg/L to about 10.0 mg/L, about 2.0 mg/L to about 8.0 mg/L, about 4.0 mg/L to about 6.0 mg/L, about 1.0 mg/L, about 2.0 mg/L, about 3.0 mg/L, about 4.0 mg/L, about 5.0 mg/L, about 6.0 mg/L, about 7.0 mg/L about 8.0 mg/L, about 9.0 mg/L, about 10.0 mg/L, about 11.0 mg/L, about 12.0 mg/L, about 13.0 mg/L, about 14.0 mg/L, about 15.0 mg/L, about 16.0 mg/L, about 17.0 mg/L, about 18.0 mg/L, about 19.0 mg/L, or about 20.0 mg/L, including all ranges derivable therebetween. The microspore-derived embryo may be contacted with the supplemented maturation medium for about 1 hour to about 72 hours, for about 12 hours to about 36 hours, for about 14 hours to about 34 hours, for about 16 hours to about 32 hours, about 18 hours to about 30 hours, about 20 hours to about 28 hours, about 22 hours to about 26 hours, or about 24 hours prior to transferring the microspore-derived embryo to the substrate, including all ranges derivable therebetween.

In certain aspects, the matured microspore-derived embryo is transferred to an agar substrate and the agar substrate comprises a plant growth regulator and about 40 mM to about 75 mM, about 45 mM to about 70 mM, about 50 mM to about 65 mM, or about 50 mM to about 60 mM of a monosaccharide solute, a disaccharide solute, or a polysaccharide solute, including all ranges derivable therebetween. Any monosaccharide, disaccharide, or polysaccharide solute may be used according to the methods and compositions provided by the present disclosure. In certain embodiments, the agar substrate comprises about 1.0% to about 1.6%, about 1.0% to about 1.4%, or about 1.2% agar, including all ranges derivable therebetween. The plant growth regulator may be any plant growth regulator which stimulates the growth and development of plant parts may be used. In one embodiment, the plant growth regulator is a gibberellic acid, non-limiting examples of which include GA1, GA3, GA4, and GA7. The concentration of the plant growth regulator, in particular embodiments is about 0.25 mg/L to about 1.0 mg/L, about 0.25 mg/L to about 0.75 mg/L, about 0.25 m/L, about 0.50 mg/L, about 0.75 mg/L, or about 1.0 mg/L, including all ranges derivable therebetween.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps. Similarly, any system or method that "comprises," "has," or "includes" one or more components is not limited to possessing only those components and covers other unlisted components.

Other objects, features, and advantages of the present disclosure are apparent from detailed description provided herein. It should be understood, however, that the detailed description and any specific examples provided, while indicating specific embodiments of the disclosure, are given by way of illustration only, since various changes and modifications within the spirit and scope of the disclosure will become apparent to those skilled in the art from this detailed description.

All references herein are incorporated herein by reference in their entirety.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1: Optimized Methods for the Maturation and Regeneration of Microspore-Derived Embryos As described herein, there is a continuing need in the art for improved methods for the maturation and regeneration of microspore-derived embryos. The present disclosure provides such methods. In one embodiment, microspore-derived embryo maturation may be improved by diluting developing torpedo stage embryos to about 200 to about 400 embryos per plate containing 15 mL medium. In another embodiment, microspore-derived embryo maturation may be improved by using a liquid NLN based maturation medium comprising about 430 mM to about 730 mM about 515 mM to about 660 mM, or about 585 mM sucrose and about 1 mg/L to about 12 mg/L or about 5 mg/L abscisic acid (ABA). In yet another embodiment, regeneration of microspore-derived embryos may be improved by using a B5 based solid regeneration medium comprising about 1.2% agar, about 58 mM sucrose, and about 0.5 mg/L GA3.

Embryo Dilution and Maturation

The optimal time to dilute the microspore-derived embryos to a concentration of about 200 to about 400 embryos per plate containing 15 mL medium is about 15 days to about 20 days after the beginning microspore culture initiation (days after culture) (DAC). At this stage, the embryos are green, individually distinguishable with the naked eye, and the majority are in the torpedo stage of development. The optimal time to dilute the embryos can vary based on genotype and initial embryo concentration (FIG. 1). During the dilution step the embryogenesis induction medium (NLN13; NLN medium containing about 380 mM sucrose) is replaced with MDE Maturation Medium (NLN medium containing about 585 mM sucrose and about 5 mg/L ABA). Plates with an initial embryo concentration of less than about 200 (FIGS. 1A and 1B) will likely need to be contacted with MDE maturation medium earlier than those with higher initial embryo concentrations (FIGS. 1C; 1D; 1E; and 1F). The microspore-derived embryos were diluted by transferring about 200 to about 400 embryos to a new plate containing 15 mL of fresh MDE Maturation media. In particular, embryos were diluted by transferring about 200 to about 400 embryos from the original stock plate to each new plate using a 10 mL sterile serological pipette. In some embodiments, the serological pipette may be broken to create a wider opening for aspirating larger embryos. During the transfer about 3 mL to about 5 mL of media is taken from the original plate to each new plate and then an appropriate volume of MDE Maturation Medium is added to each new plate to bring the total volume to 15 ml. If the original plates have a starting concentration of about 200 embryos per plate or less, then the media of the original plate is replaced with MDE Maturation Medium without embryo dilution. Following dilution and/or media replacement, plates were returned to 100 μmol fluorescent light for a 16 hour photoperiod, 25° C. day and night with an orbital shaker set to 60 RPM, and cultured to about 28 to about 30 DAC before transferring to a solid regeneration medium.

Regeneration/Germination

Figure 2:
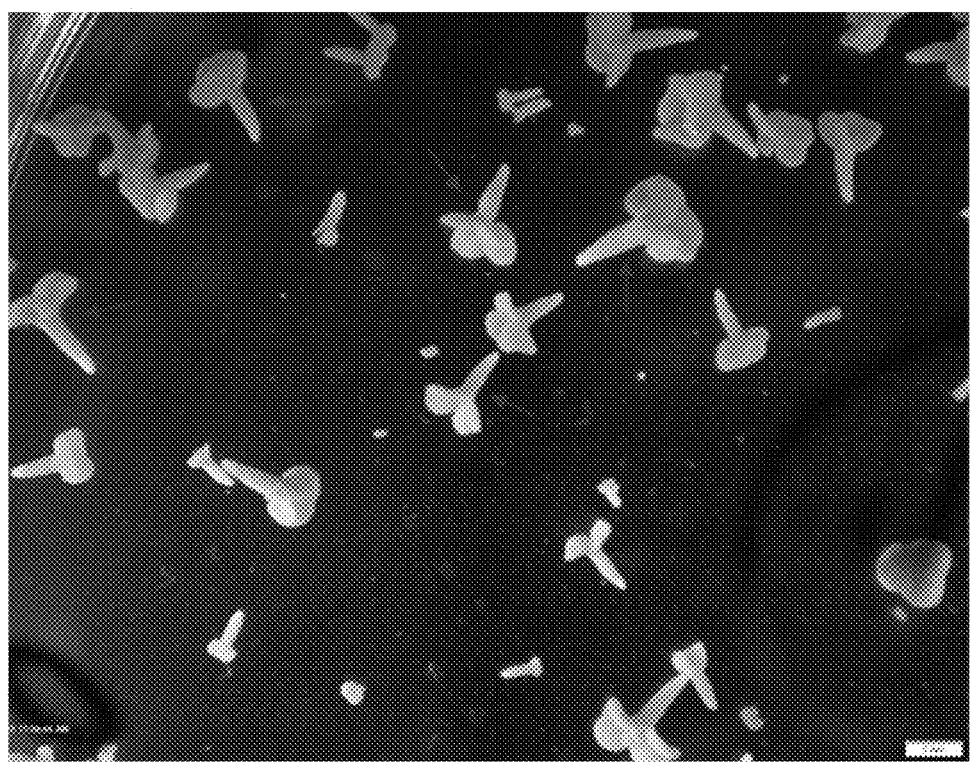
FIG. 2: Shows maturated microspore-derived embryos at about 28 DAC having an average length of about 2.5 mm. The arrows point to examples of embryos which are appropriate for transfer to MDE regeneration medium.

At about 28 to about 30 DAC, most embryos were ready to transfer to a regeneration medium for plant regeneration. Embryos with fully developed cotyledons and no signs of browning or anthocyanin accumulation (FIG. 2) were selected for transfer to MDE Regeneration Medium (B5 containing about 1.2% agar, about 58 mM sucrose, and about 0.5 mg/L GA3). At this stage, embryos are typically about 2.5 mm to about 4 mm in length. Matured embryos can be stored from about 0 days to about 8 weeks in the maturation media under cold storage before transferring to plant regeneration plates. Embryos were transferred using sterile forceps to gently push the embryo cotyledons into the agar surface of the MDE regeneration medium in an upright orientation. One regeneration plate accommodates up to about 16 embryos. Regeneration plates were sealed with micropore tape and placed in an incubator set to 24° C., 16 hour photoperiod with 100 μmol/m$^2$/s light for about 28 days to about 30 days.

Transfer of Regenerated Plantlets to Soil

Figure 3:
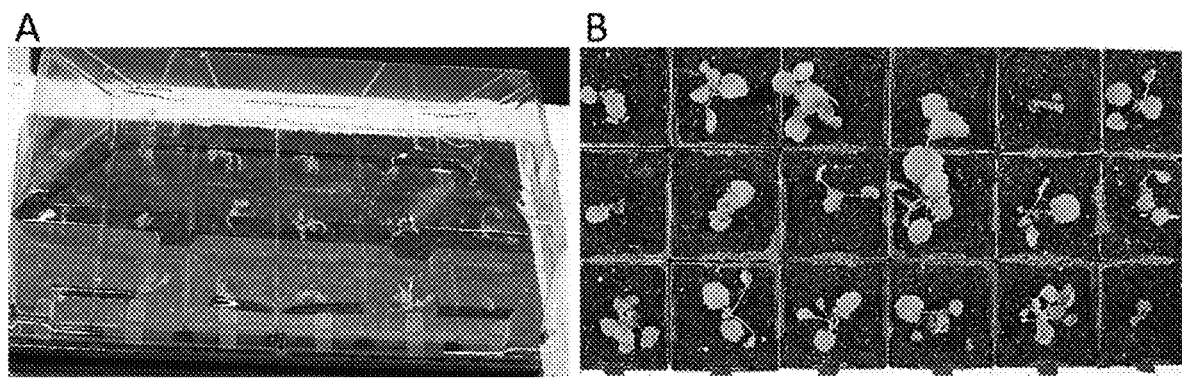
FIG. 3: Shows regenerated plantlets following transfer from regeneration medium to a soil mix.

Following 4 weeks of culture in contact with MDE Regeneration Medium, regenerated plantlets were transferred to pre-wet PGX soil mix. In particular, plantlets were removed by gently holding the regenerated plantlets by the base of their shoots and slowly pulling them from the MDE Regeneration Medium, care was taken to preserve as much of the root as possible. Removed plantlets were placed in the pre-wet PGX soil mix at a sufficient depth to cover the roots and soil was then pinched around the roots. Potted plantlets were then placed in a sub-irrigation tray. The pots were covered with a humidome for the first week. Plantlets were grown in a growth chamber at 300 μmol/m2/s light for a 16 hour photoperiod, 20° C. day, 15° C. night, and 50% relative humidity. FIG. 3A shows the plantlets immediately after transfer to the soil mix and FIG. 3B shows plantlets grown for one week after transfer to the soil mix.

Example 2: Methods for Improved Maturation and Regeneration of Microspore-Derived Embryos in Recalcitrant Canola Microspore-derived embryos from 15 proprietary, recalcitrant $F_1$ canola lines were analyzed in a series of protocols to identify optimized conditions for maturation and regeneration. The tested lines included 8 female (B) and 7 male (R) lines, and each line was previously identified as recalcitrant in DH experiments. The protocols tested are summarized in in Table 1. Briefly, the control protocol represents the standard canola microspore-derived embryo induction and regeneration method without an extra maturation treatment step used in the canola DH pipeline, which includes culture with NLN13 Medium (NLN Medium containing about 380 mM sucrose) without embryo dilution, and regeneration in contact with a B5 regeneration medium containing about 0.1 mg/L BAP, about 0.1 mg/L GA3, about 58 mM sucrose, and about 0.8% agar. Test Protocol 1 includes embryo dilution at the torpedo stage to about 200 to about 400 embryos per plate with NLN13 Medium and regeneration in contact with MDE Regeneration Medium (B5 containing about 1.2% agar, about 58 mM sucrose, and about 0.5 mg/L GA3). Test Protocol 2 includes embryo dilution at the torpedo stage to about 200 to about 400 embryos per plate with NLN13 Medium containing about 5 mg/L ABA and regeneration in contact with MDE Regeneration Medium. Test Protocol 3 includes dilution in NLN20 Maturation Medium (NLN Medium containing about 585 mM sucrose) and regeneration in contact with MDE Regeneration Medium. Test protocol 4 includes embryo dilution in MDE Maturation Medium (NLN medium containing about 585 mM sucrose and about 5 mg/L ABA). In all protocols which include embryo dilution, the dilution is performed when the embryos reach the torpedo stage. At this stage almost all of the microspore-derived embryos are already formed.

TABLE 1

Summary of Protocols Analyzed to Determine Optimized Conditions for Maturation and Regeneration of Microspore-Derived Embryos from Recalcitrant Canola.

| | Key optimization factors | |
| --- | --- | --- |
| Protocol | Dilution step | Regeneration Media |
| Control | NLN13, no standardized dilution or medium refresh | B5, 0.8% agar + 0.1 mg/L BAP + 0.1 mg/L GA3, 58 mM sucrose |
| Test Protocol 1 | Dilute embryos to 200-400 embryos/plate with NLN13 at torpedo stage | MDE Regeneration Medium (B5, 1.2% agar, 0.5 mg/L GA3, 58 |

TABLE 1-continued

Summary of Protocols Analyzed to Determine Optimized Conditions for Maturation and Regeneration of Microspore-Derived Embryos from Recalcitrant Canola.

| | Key optimization factors | |
|---|---|---|
| Protocol | Dilution step | Regeneration Media |
| Test Protocol 2 | Dilute embryos to 200-400 embryos/plate with NLN13 + 5 mg/L ABA at torpedo stage | mM sucrose) |
| Test Protocol 3 | Dilute embryos to 200-400 embryos/plate with NLN20 at torpedo stage | |
| Test Protocol 4 | Dilute embryos to 200-400 embryos/plate MDE Maturation Medium at torpedo stage | |

Figure 4:
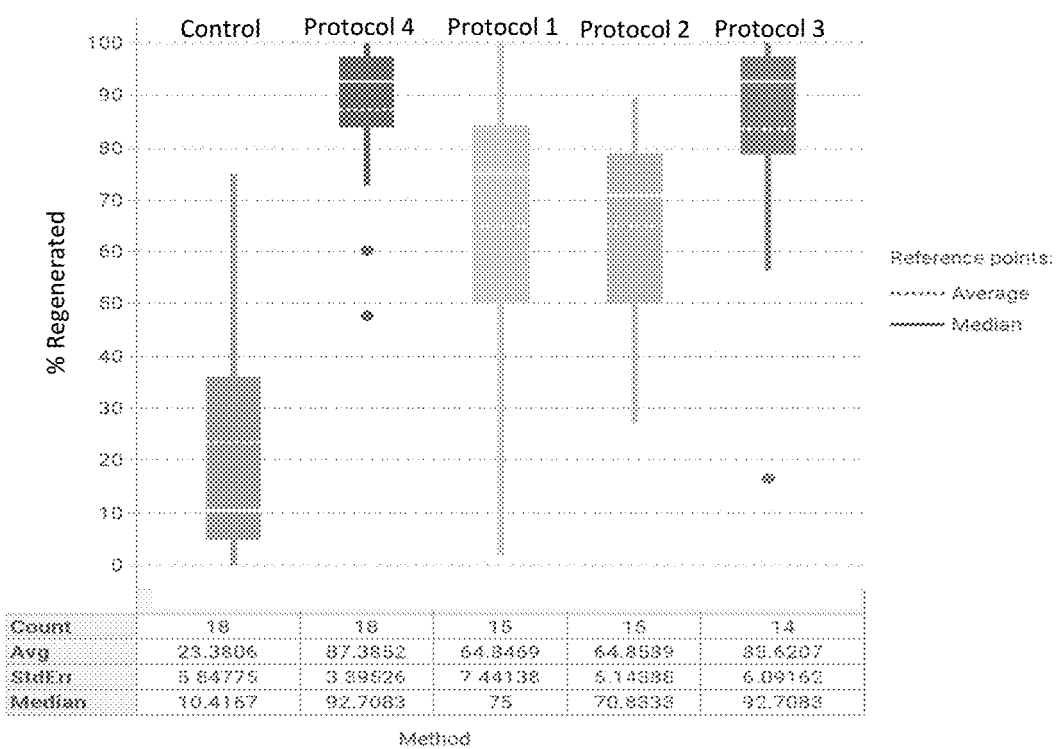
FIG. 4: Demonstrates the effects of embryo dilution, sucrose concentration, abscisic acid addition, BAP removal, GA3 concentration, and agar concentration on the regeneration rate of microspore-derived embryos from recalcitrant canola lines in culture-based protocols.

As shown in FIG. 4, embryo dilution at the torpedo stage in combination with regeneration in contact with MDE Regeneration Medium (Test Protocol 1) increased the regeneration rate from about 23% to about 65% compared to control. The addition of ABA to Test Protocol 1 (Test Protocol 2) did not further improve the average regeneration rate, but did this addition did decrease variance by 2.3% (FIG. 4). Embryo dilution in NLN20 Medium in combination with regeneration in contact with MDE Regeneration Medium (Test Protocol 3) increased the regeneration rate from about 23% to about 84% compared to the control (FIG. 4). The addition of ABA to Test Protocol 3 (Test Protocol 4) increased the regeneration rate from about 23% to about 87% (FIG. 4).

Example 3: Methods for Improved Maturation and Regeneration of Microspore-Derived Embryos in Recalcitrant Winter Oilseed Rape Microspore-derived embryos from 10 proprietary, recalcitrant $F_1$ winter oilseed rape lines were analyzed to determine if the optimized conditions for maturation and regeneration identified for recalcitrant canola were also optimized for winter oilseed rape. The tested lines included 9 female (B) lines and 1 male (R) line, and each line was previously identified as recalcitrant in DH experiments. The protocols tested are summarized in in Table 2.

TABLE 2

Summary of Protocols Analyzed to Determine Optimized Conditions for Maturation and Regeneration of Microspore-Derived Embryos from Recalcitrant Winter Oilseed Rape.

| Step | Control Method | Optimized Method |
|---|---|---|
| Embryo Dilution/Refreshing | Do not dilute embryos or refresh media | Dilute embryos/refresh media 15-20 DAC. Change culture media to NLN20 + 5 mg/L ABA |
| Embryo Transfer Timing | 28-30 days after culture | |
| Regeneration Medium | B5 + 58 mM sucrose + 1.2% agar + 1 mg/L GA3 + 37 mg/L CaCl2 + 128 mg/L MgSO4 | B5 + 58 mM sucrose + 1.2% agar + 0.5 mg/L GA3 |
| Regeneration Conditions | 24° C., 16 h daylight | 24° C., 16 h daylight |
| Regeneration Timing | 28 days-30 days | 28 days-30 days |
| Total Time | 8-9 weeks | 8-9 weeks |

Figure 5:
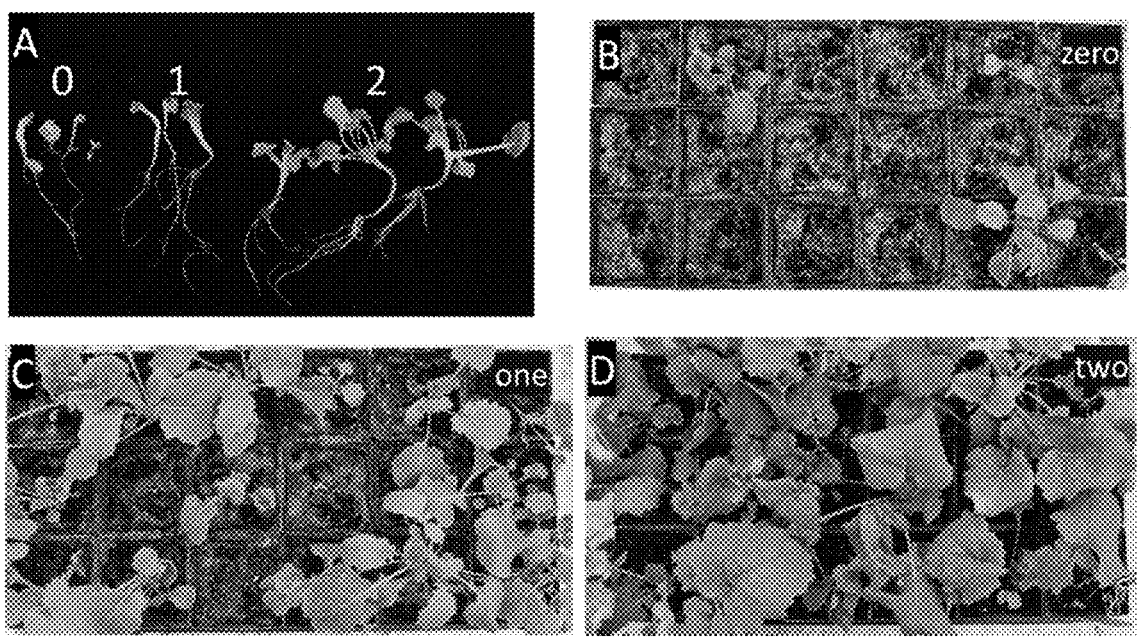
FIG. 5: Shows a scoring system for assessing the regeneration quality of plantlets derived from microspore-derived embryos.

The quality of regeneration was categorized in this experiment using a novel scoring system. Microspore-derived embryos without successful regeneration were assigned a "0" score, these embryos did not have good root development and some developed callus or were necrotized with arrested development (FIG. 5A). Embryos with a "0" score were not suitable for transfer to soil, and most did not survive the transfer (FIG. 5B). Regenerated plantlets having good root development, underdeveloped shoots, and a healthy green color with a clear apical meristem were assigned a "1" score (FIG. 5A). These plantlets were found to have about a 50% to about an 80% survival rate when transferred to soil (FIG. 5C). Regenerated plantlets having well-developed shoots with multiple leaves and roots with lateral roots and root hairs were assigned a "2" score (FIG. 5A). These plantlets have about a 100% survival rate when transferred to soil (FIG. 5D).

Figure 6:
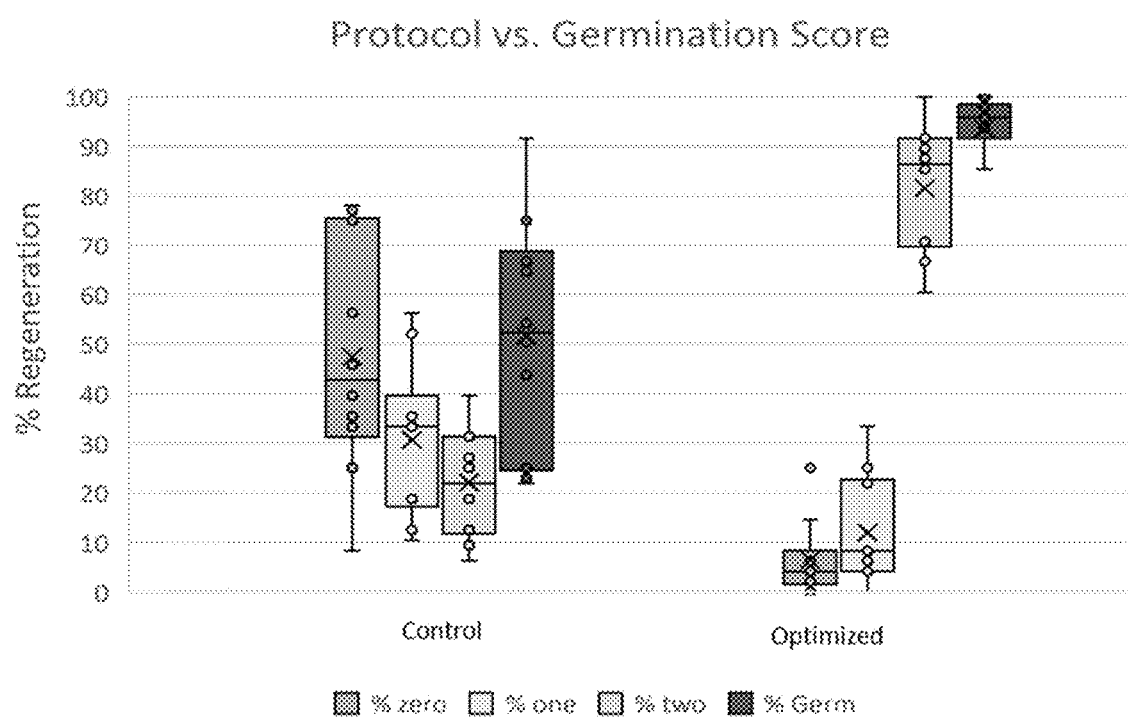
FIG. 6: Demonstrates improved maturation and regeneration of winter oilseed rape microspore-derived embryos matured and regenerated using an optimized method.

As shown in FIG. 6, the optimized conditions identified for maturation and regeneration of microspore-derived embryos from recalcitrant canola lines also performed well with embryos derived from recalcitrant winter oilseed rape lines. The use of these optimized conditions increased the average total regeneration rate to about 93.6% compared to an average total regeneration rate of about 51.2% obtained using the control protocol in a side-by-side comparison (labeled as "% Germ" black bar in FIG. 6). Furthermore, the use of these optimized conditions produced significantly more high quality plantlets having a "2" score compared to the control method (FIG. 6). The ratio of plantlets having a "0", "1", or "2" score is 45%:35%:25% using control method, while this ratio is 5%:9%:86% using the optimized method.

Example 4: Culture-Free Methods for the Maturation and Regeneration of Microspore-Derived Embryos As described herein, there is a continuing need in the art for improved methods for the maturation and regeneration of microspore-derived embryos. Prior to the present disclosure, all methods for microspore-derived embryo maturation and regeneration included an in vitro culture step, where embryos are placed on solid agar plates and incubated in a sterile environment to establish plantlets. This process is laborious and expensive. Furthermore, there are many well-known technical challenges associated with tissue culture-based plant regeneration techniques, such as heavy callusing, multiple shoot development, and poor root development. These tissue culture-based methods, however, have been historically preferred for microspore-derived embryo maturation and regeneration because microspore-derived embryos are fragile, tender, and immature. Prior to the methods described in the present disclosure, microspore-derived embryos placed directly into soil would not survive.

The present example provides culture-free methods for the maturation and regeneration of microspore-derived embryos, which eliminate the tedious and often costly sterile tissue culture steps associated with other embryo maturation and regeneration methods. The methods include, in some embodiments, steps of embryo dilution, embryo maturation, and culture-free regeneration.

Embryo Dilution and Maturation

The optimal time to dilute the microspore-derived embryos to a concentration of about 200 to about 400 embryos per plate containing 15 mL medium is about 15 days to about 20 days after the beginning microspore culture initiation (days after culture) (DAC). At this stage, the embryos are green, individually distinguishable with the naked eye, and the majority are in the torpedo stage of development. During the dilution step the embryogenesis induction medium (NLN13) is replaced with MDE Maturation Medium. The microspore-derived embryos were diluted by transferring about 200 to about 400 embryos to a new plate containing 15 mL of MDE Maturation Medium. If the original plates have a starting concentration of about 200 embryos per plate or less, then the media of the original plate is replaced with MDE Maturation Medium without embryo dilution. Following dilution and/or media replacement, plates were returned to 100 µmol fluorescent light for a 16 hour photoperiod, 25° C. day and night with an orbital shaker set to 60 RPM, and cultured to about 28 to about 30 DAC to reach a matured cotyledon stage before transferring to a solid regeneration medium. Matured embryos can be stored from about 0 days to about 8 weeks in the maturation media under cold storage followed by indole-3-butyric acid (IBA) treatment. 5 mg/L of indole-3-butyric acid (IBA) was added to each embryo plate. IBA is an auxin, which is known can promote root development. Incubation with IBA for about 1 to about 24 hours accelerates rooting and increases plantlet survival and establishment in soil.

Culture-Free Regeneration

Following incubation with IBA for about 1 to about 24 hours (at about 30 to about 35 DAC), embryos were transferred to pre-moistened Pro-mix PGX soil in 8.9 cm square pots containing about 0.59 kg/m$^3$ gypsum. The radicle side of the embryos were gently pushed into the surface of the soil and the cotyledons were left exposed. Pots were placed in a tray, covered with a humidome to maintain a relative humidity of about 65% to about 95%, and placed in a growth chamber under the following conditions: 16 hour photoperiod, 20° C. day, 15° C. night, and 300 µmol/m$^2$/s light. After one week, one end of the humidome was raised 2.54 cm above the surface of the pots decreasing the relative humidity to about 50% to about 65%. After one additional week of incubation, the humidome was removed and the regenerating plantlets were watered by sub-irrigation as needed. Regeneration rate was measured after 28 days of incubation.

Example 5: Culture-Free Methods for the Maturation and Regeneration of Microspore-Derived Embryos Significantly Reduce the Time and Cost Associated with Plant Regeneration In an initial experiment, microspore-derived embryos were transferred directly to soil pots under standard sowing conditions. In this initial experiment, only 1 out of 48 embryos survived. Therefore, in order to identify optimized conditions for the culture-free maturation and regeneration of micropore-derived embryos, the following parameters were varied and analyzed: 1) the relative humidity at which the embryos were incubated following transfer to soil; 2) incubation with MDE Maturation Medium prior to transfer to soil; and 3) pre-treatment of embryos with plant growth regulators prior to transfer to soil.

Microspore-derived embryos from 10 proprietary canola lines were analyzed in a series of protocols to identify optimized conditions for culture-free maturation and regeneration. The protocols tested are summarized in in Table 3. Briefly, the control protocol represents the standard canola microspore-derived embryo induction and regeneration method used in the canola DH pipeline, which includes culture with NLN13 Medium (NLN Medium containing about 380 mM sucrose) without embryo dilution, and regeneration in contact with a B5 regeneration medium containing about 0.1 mg/L BAP, about 0.1 mg/L GA3, about 58 mM sucrose, and about 0.8% agar. Test Protocol 1 includes embryo dilution at the torpedo stage to about 200 to about 400 embryos per plate with NLN13 Medium and regeneration in contact with pre-moistened Pro-mix PGX at high relative humidity about (95%). Test Protocol 2 includes embryo dilution at the torpedo stage to about 200 to about 400 embryos per plate with MDE Maturation Medium and regeneration in contact with pre-moistened Pro-mix PGX at high relative humidity. Test Protocol 3 includes embryo dilution at the torpedo stage to about 200 to about 400 embryos per plate with MDE Maturation Medium followed by the addition of 5 mg/L IBA 24 hours prior to transfer to pre-moistened Pro-mix PGX at high relative humidity. To create high relative humidity conditions embryos were placed in soil at 30 DAC and a humidome was utilized to maintain a high relative humidity.

TABLE 3

Summary of Protocols Analyzed to Determine Optimized Conditions for Culture-Free Maturation and Regeneration of Microspore-Derived Embryos from Recalcitrant Canola.

| | Key optimization factors | |
| --- | --- | --- |
| Protocol | Dilution step | Regeneration Media |
| Control | NLN13, no standardized dilution or medium refresh | B5, 0.8% agar + 0.1 mg/L BAP + 0.1 mg/L GA3, 58 mM sucrose |
| Test Protocol 1 | Dilute embryos to 200-400 embryos/plate with NLN13 at torpedo stage | Pre-moistened Pro-mix PGX; high relative humidity |
| Test Protocol 2 | Dilute embryos to 200-400 embryos/plate MDE Maturation Medium at torpedo stage | Pre-moistened Pro-mix PGX; high relative humidity |
| Test Protocol 3 | Dilute embryos to 200-400 embryos/plate MDE Maturation Medium at torpedo stage + 5 mg/L IBA 24 hours prior to transfer | Pre-moistened Pro-mix PGX; high relative humidity |

Figure 7:
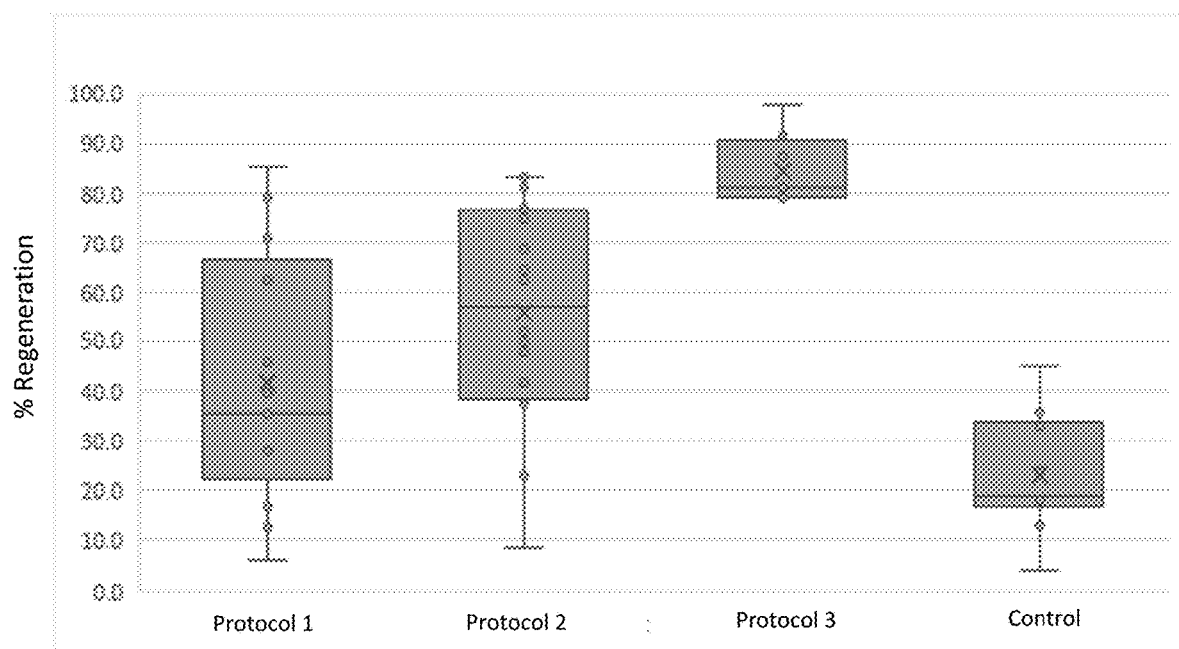
FIG. 7: Demonstrates the effect of relative humidity, sucrose concentration, abscisic acid addition, and indole-3-butyric acid addition on the regeneration rate of microspore-derived embryos from canola lines in culture-free protocols.

As shown in FIG. 7, embryo dilution at the torpedo stage with NLN13 Medium in combination with regeneration in contact with pre-moistened Pro-mix PGX at high relative humidity (Test Protocol 1) increased the average regeneration rate to about 41%, however, these results were highly variable between genotypes. Embryo dilution at the torpedo stage with MDE Maturation Medium in combination with regeneration in contact with pre-moistened Pro-mix PGX at high relative humidity (Test Protocol 2) increased the average regeneration rate to about 48% (FIG. 7). The addition of 5 mg/L IBA 24 hours prior to transfer to pre-moistened pro-mix PGX at high relative humidity (Test Protocol 3) increased the average regeneration rate to about 85.4% (FIG. 7). The abscisic acid and the increased sucrose concentration found in the MDE Maturation Medium stimulate the stress response and improve embryo development prior to transfer to soil. The addition of IBA to the MDE Maturation Medium improves rooting.

Figure 8:
FIG. 8: Shows the development of plantlets regenerated from winter oilseed rape microspore-derived embryos.

As shown in FIG. 8, the optimized culture-free based method developed for the maturation and regeneration of canola microspore-derived embryos (Table 3, protocol 3) also demonstrates good results in winter oilseed rape. In particular, FIG. 8A shows established plantlets regenerated using the optimized agar plate culture-based method for winter oilseed rape as described in Table 2, column 3 at approximately 30 DAT. FIG. 8B shows established plantlets regenerated using the culture-free method described in Table 3, Test Protocol 3 at approximately 30 DAT. On average, plantlets regenerated using the culture-free method are approximately two weeks farther in development compared to those of the same genotype regenerated using the culture-based method. This trend is consistent across genotypes.

Figure 9:
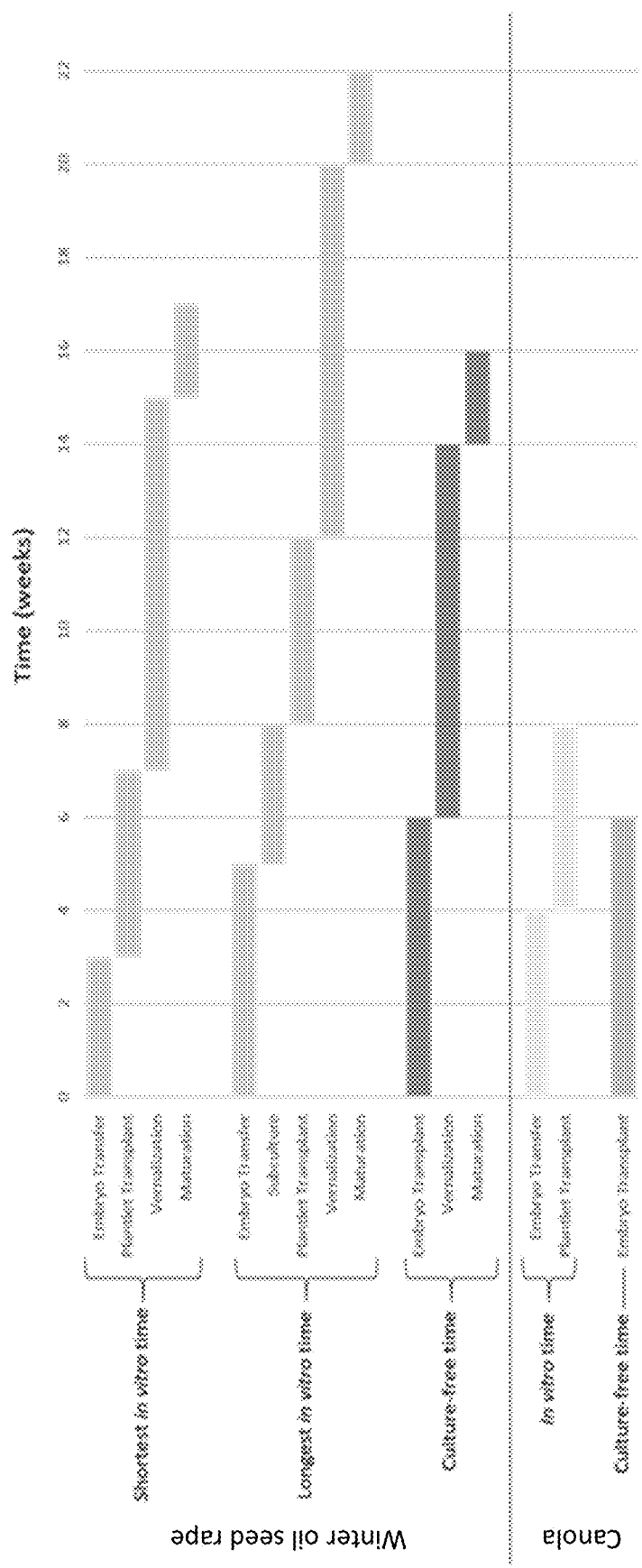
FIG. 9: Shows a timeline comparing the estimated time from transfer of microspore-derived embryos to plantlet flowering for the culture-based and culture-free methods of plant regeneration for winter oilseed rape and canola.
Figure 10:
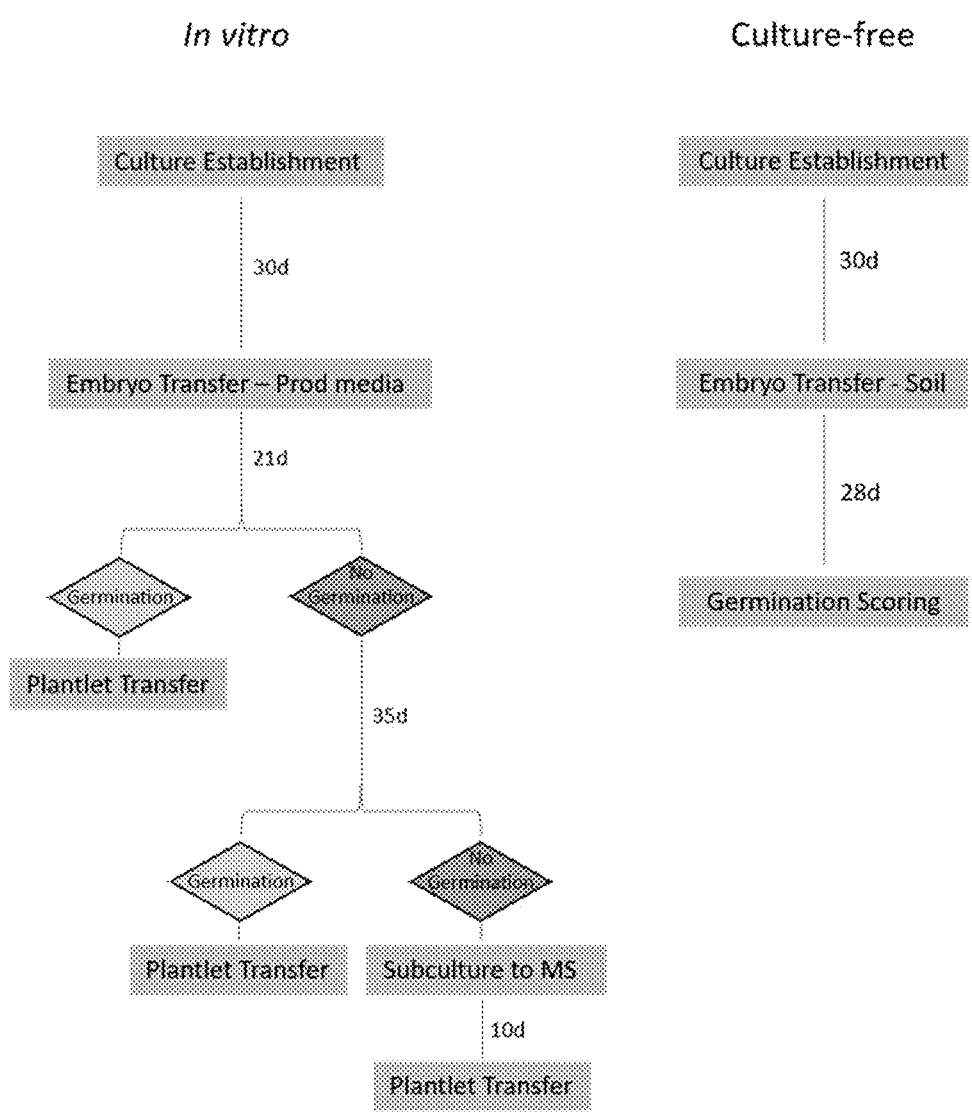
FIG. 10: Shows a comparison of the workflow for the winter oilseed rape culture-based and culture-free methods of plantlet regeneration from microspore-derived embryos.

As shown in FIG. 9, the regeneration of plantlets from microspore-derived embryos using culture-based methods takes approximately 4-5 weeks and sometimes even longer, if plant establishment requires further shooting and/or rooting processes. Furthermore, after developed plantlets are transferred from agar plates into soil, they often take about one week to recover before they resume growing. For canola, the culture-free regeneration method can shorten the time to $DH_1$ seed set by about two weeks. Many winter oilseed rape lines exhibit callusing during culture-based regeneration and often require subculturing prior to transfer to soil. A workflow comparison of winter oilseed rape DH production using culture-based and culture-free regeneration methods is shown in FIG. 10. Therefore, culture-free regeneration of plantlets from microspore-derived embryos may shorten the time to winter oilseed rape $DH_1$ seed set but about 4 to about 6 weeks (FIG. 9). In summary, the culture-free regeneration method described in the present example, shortens the cycle time to $DH_1$ seed set by up to 6 weeks and reduces the labor and resource inputs by 50% or more compared to traditional culture-based methods.

What is claimed is:

1. A method of generating a plantlet, the method comprising:
   (a) contacting a plurality of microspore-derived embryos with a liquid maturation medium at a concentration of about 5 to about 50 microspore-derived embryos per mL maturation medium for a time period sufficient to produce at least one matured microspore-derived embryo, wherein the maturation medium comprises a first plant hormone and about 430 mM to about 880 mM of a monosaccharide solute, a disaccharide solute, or a polysaccharide solute;
   (b) transferring the matured microspore-derived embryo to a substrate; and
   (c) regenerating the plantlet from the matured microspore-derived embryo.

2. The method of claim 1, the method comprising first contacting the plurality of microspore-derived embryos with the maturation medium when the microspore-derived embryos are at a torpedo stage to a cotyledon stage of development.

3. The method of claim 1, the method comprising transferring the matured microspore-derived embryo to the substrate when the matured microspore-derived embryo is at a cotyledon stage of development.

4. The method of claim 1, wherein the substrate is selected from the group consisting of a solid substrate, a soil substrate, an agar substrate, and a soilless substrate.

5. The method of claim 1, wherein said transferring comprises transferring the matured microspore-derived embryo directly to a soil substrate or a soilless substrate.

6. The method of claim 1, where in the first plant hormone is an abscisic acid receptor agonist.

7. The method of claim 6, wherein the abscisic acid receptor agonist is selected from the group consisting of abscisic acid, an abscisic acid analog, an abscisic acid derivative, pyrabactin, julolidine and fluorine containing ABA receptor activator 1, and julolidine and fluorine containing ABA receptor activator 2.

8. The method of claim 1, wherein the concentration of the first plant hormone is about 1.0 mg/L to about 20.0 mg/L.

9. The method of claim 1, wherein the monosaccharide solute, the disaccharide solute, or the polysaccharide solute is selected from the group consisting of glucose, fructose, galactose, sucrose, lactose, and mannose.

10. The method of claim 1, further comprising culturing the plurality of microspore-derived embryos in an induction medium prior to said step (a).

11. The method of claim 1, the method further comprising contacting the plurality of microspore-derived embryos with a supplemented maturation medium prior to transferring the matured microspore-derived embryo to the substrate, wherein the supplemented maturation medium comprises a second plant hormone.

12. The method of claim 11, the method comprising contacting the plurality of microspore-derived embryos with the supplemented maturation medium for about 1 hour to about 72 hours or about 12 hours to about 36 hours prior to said transferring.

13. The method of claim 11, wherein the second plant hormone is an auxin.

14. The method of claim 13, wherein the auxin is selected from the group consisting of indole-3-butyric acid, 2,4-dichlorophenoxy-acetic acid (2,4-D), 4-amino-3,5,6-trichloro-picolinic acid (picloram), indole-3-acetic acid (IAA), naphthalene acetic acid (NAA), 4-chlorophenoxy acetic acid or p-chloro-phenoxy acetic acid (4-CPA or pCPA), 2,4,5-trichloro-phenoxy acetic acid (2,4,5-T), 2,3,5-triiodobenzoic acid (TIBA), phenylacetic acid (PAA), and 3,6-dichloro-2-methoxy-benzoic acid (dicamba).

15. The method of claim 11, wherein the concentration of the second plant hormone is about 1.0 mg/L to about 20.0 mg/L.

16. The method of claim 1, wherein the substrate is an agar substrate, and the agar substrate comprises a plant growth regulator and about 40 mM to about 75 mM of a monosaccharide solute, a disaccharide solute, or a polysaccharide solute.

17. The method of claim 16, wherein the monosaccharide solute, the disaccharide solute, or the polysaccharide solute is selected from the group consisting of glucose, fructose, galactose, sucrose, lactose, and mannose.

18. The method of claim 16, wherein the agar substrate further comprises about 1.0% to about 1.6% agar.

19. The method of claim 16, wherein the concentration of the plant growth regulator is about 0.25 mg/L to about 1.0 mg/L.

20. The method of claim 16, wherein the plant growth regulator is a gibberellic acid.

21. The method of claim 20, wherein the gibberellic acid is selected from the group consisting of GA1, GA3, GA4, and GA7.

22. The method of claim 16, further comprising transferring the plantlet from the agar substrate to a soil substrate or to a soilless substrate.

23. The method of claim 1, wherein the plurality of microspore-derived embryos are derived from a species of the genus *Brassica* or of the genus *Capsicum*.

* * * * *